United States Patent
Schmitt et al.

(10) Patent No.: US 9,918,464 B2
(45) Date of Patent: Mar. 20, 2018

(54) STRAW FOR THE STORAGE OF A PREDETERMINED DOSE OF A LIQUID-BASED SUBSTANCE, IN PARTICULAR A BIOLOGICAL SUBSTANCE

(71) Applicant: IMV TECHNOLOGIES, Saint Ouen sur Iton (FR)

(72) Inventors: Eric Schmitt, Villaines-la-Juhel (FR); Jean-Charles Gorges, Chenay (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 409 days.

(21) Appl. No.: 14/627,405

(22) Filed: Feb. 20, 2015

(65) Prior Publication Data

US 2015/0237848 A1    Aug. 27, 2015

(30) Foreign Application Priority Data

Feb. 21, 2014  (FR) .................................. 14 51418

(51) Int. Cl.
| C12M 1/00 | (2006.01) |
| C12M 3/00 | (2006.01) |
| A01N 1/02 | (2006.01) |
| A61D 19/02 | (2006.01) |

(52) U.S. Cl.
CPC ......... A01N 1/0268 (2013.01); A61D 19/024 (2013.01)

(58) Field of Classification Search
CPC .. A61D 19/022; A61D 19/021; A61D 19/024; A01N 1/0268
USPC ...................................... 435/307.1
See application file for complete search history.

(56) References Cited

U.S. PATENT DOCUMENTS

| 5,868,178 A | 2/1999 | Lecointe |
| 6,203,489 B1 | 3/2001 | Mori et al. |
| 6,416,611 B1 | 7/2002 | Saint-Ramon et al. |
| 2001/0014376 A1 | 8/2001 | Saint-Ramon et al. |
| 2002/0183653 A1 | 12/2002 | Saint-Ramon et al. |
| 2002/0188222 A1* | 12/2002 | Saint-Ramon ....... A61D 19/024 600/573 |

(Continued)

FOREIGN PATENT DOCUMENTS

| CN | 1828301 A | 9/2006 |
| EP | 0873726 A1 | 10/1998 |
| FR | 995878 | 12/1951 |

(Continued)

*Primary Examiner* — Nathan Bowers
*Assistant Examiner* — Lydia Edwards
(74) *Attorney, Agent, or Firm* — Browdy and Neimark, PLLC

(57) ABSTRACT

The straw comprises a tube (11) having a swelling plug (15) provided with a fibrous support agent and a swelling agent combined with the support agent and configured, at least close to a second end (18) of the swelling plug, after a liquid-based substance has come up against its second end, to be in a state of swelling constrained by said tube such that if a first part (26) of the swelling plug of length comprised between 2 mm and 3 mm starting from its second end has come out of the tube via a second end (14) of the tube, whereas a second part of the swelling plug remains in the tube, the first part of the swelling plug becomes decompacted and expands with the second end of the swelling plug which assumes a diameter (d) at least equal to one and a half times the inner diameter of the tube.

15 Claims, 3 Drawing Sheets

(56) References Cited

U.S. PATENT DOCUMENTS

2006/0177352 A1 8/2006 Ziegmann et al.
2009/0246782 A1* 10/2009 Kelso ............... B01L 3/502761
　　　　　　　　　　　　　　　　　　　　　　　　　435/6.16

FOREIGN PATENT DOCUMENTS

| | | |
|---|---|---|
| FR | 2044797 A1 | 2/1971 |
| FR | 2651676 A1 | 3/1991 |
| FR | 2753367 A1 | 3/1998 |
| FR | 2771285 A1 | 5/1999 |
| FR | 2781662 A1 | 2/2000 |
| FR | 2784572 A1 | 4/2000 |
| FR | 2824255 A1 | 11/2002 |
| FR | 2824256 A1 | 11/2002 |
| GB | 669265 | 4/1952 |
| WO | 2010070533 A1 | 6/2010 |

* cited by examiner

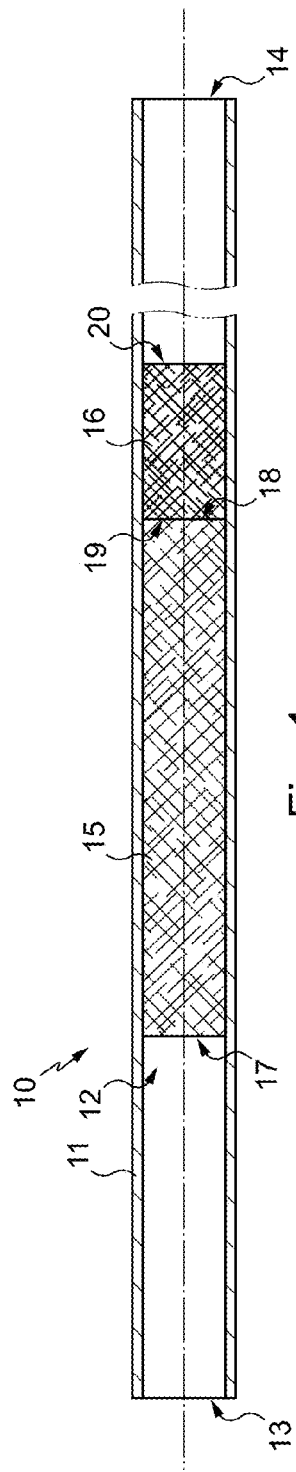
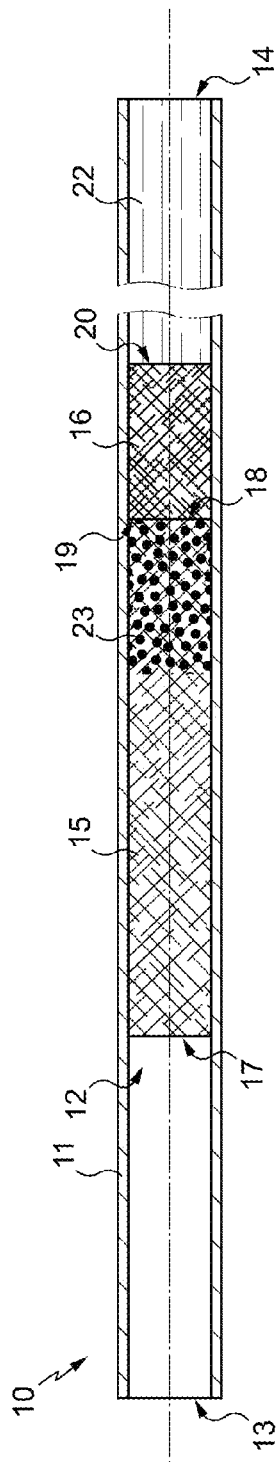
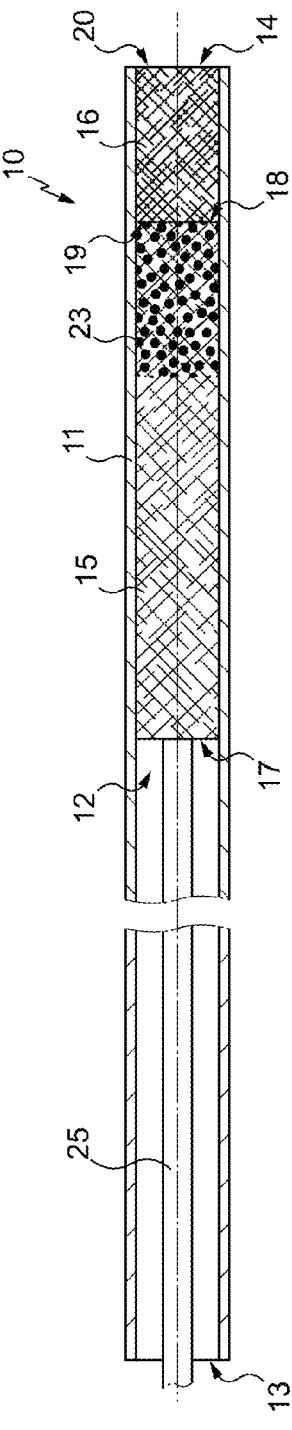

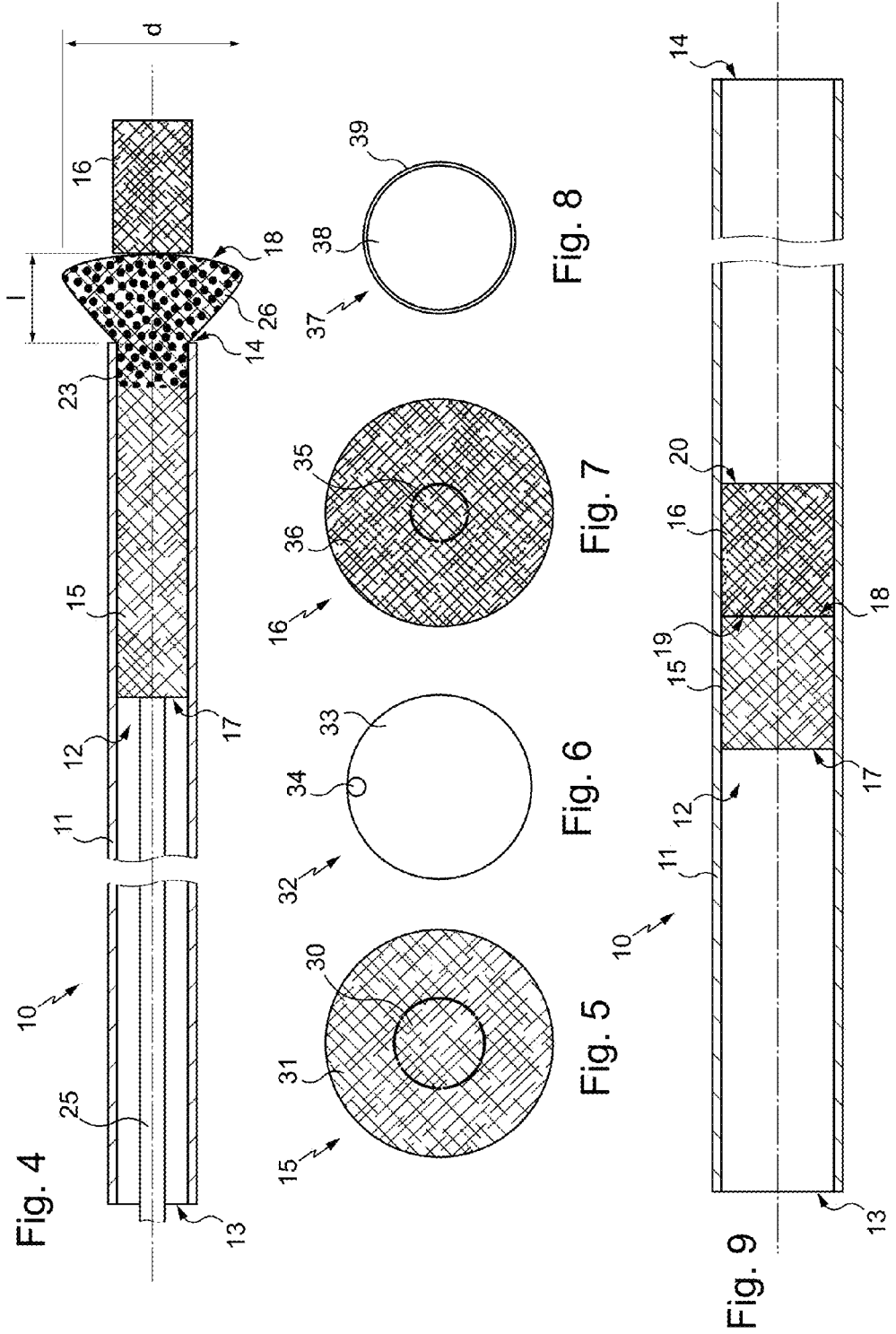

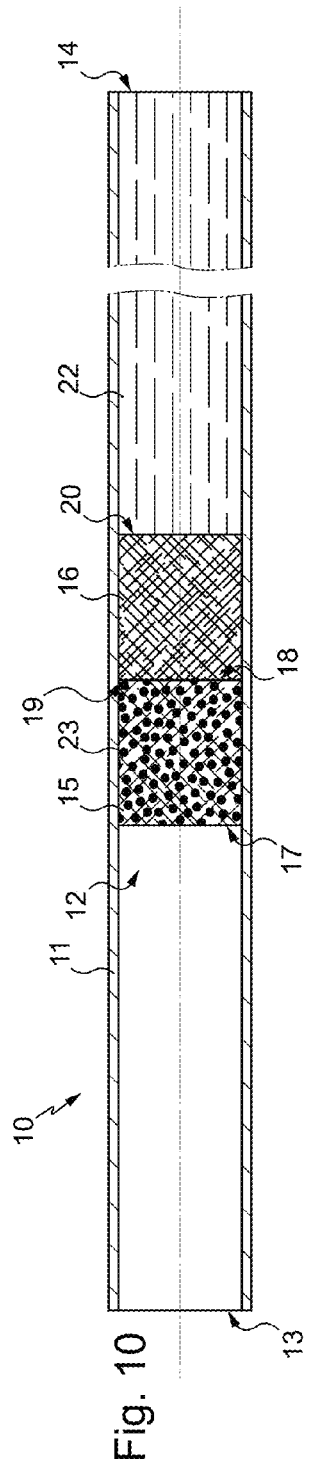
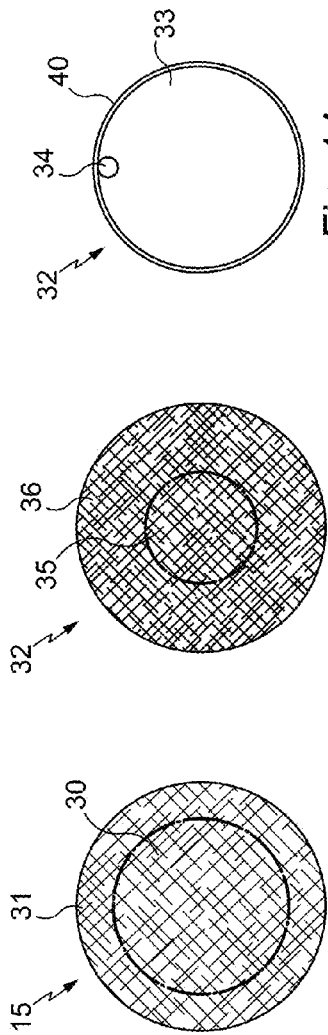
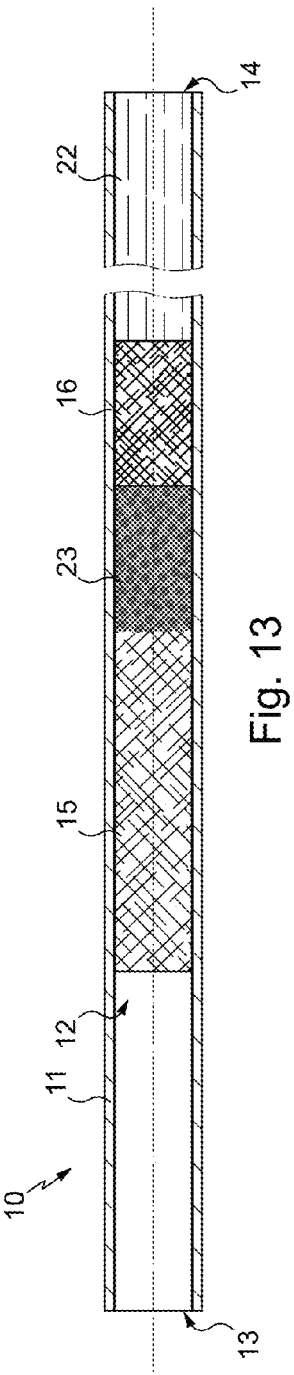

STRAW FOR THE STORAGE OF A PREDETERMINED DOSE OF A LIQUID-BASED SUBSTANCE, IN PARTICULAR A BIOLOGICAL SUBSTANCE

The invention relates to straws for the storage of a predetermined dose of liquid-based substance, in particular a biological substance, for example pure or diluted animal semen or a storage medium containing embryos.

It is known that such a straw is conventionally formed by a thin tube, having for example an inner diameter of 1.6 or 2.5 mm, and by a stopper inserted in the thin tube.

In the filled state, the stopper is arranged close to a first end of the tube and the dose of substance is arranged in the straw between the stopper and the second end of the tube.

In order to fill the straw, the first end of the tube, close to the stopper, is placed in communication with a vacuum source, while the second end is placed in communication with a vessel containing the substance to be introduced into the straw. The air initially contained between the stopper and the second end is sucked through the stopper while the substance moves forward into the tube until it reaches the stopper, which it cannot pass because the stopper becomes liquid-tight.

If necessary, after filling, the straw is welded close to one or both of its ends and is stored cold.

In order to empty the straw, if necessary after cutting off the welded end portions and thawing, a rod is inserted into the tube via the end closest to the stopper, until it rests against the stopper. Using this rod, the stopper is made to slide in the manner of a piston towards the end furthest from the stopper, so that the dose of substance initially contained in the straw is expelled through this end.

Straw stoppers are generally of the three-part type originally described in French patent 995.878, corresponding to British patent 669,265, i.e. formed by two plugs made from a fibrous substance enclosing a powder which, on contact with a liquid, is transformed into an impermeable paste or gel adhering to the wall of the tube so that the stopper is liquid-tight.

French patent application 2 651 676 proposes a stopper constituted by a first plurality of fibres and a second plurality of fibres combined together by braiding, the first plurality of fibres being constituted by fibres that can be polymerized under the action of the liquid and the second plurality of fibres being constituted by fibres that conduct liquid by capillary action. The fibres that can be polymerized under the action of the liquid are made from the same material as the powder of the conventional three-part stoppers.

French patent 2 753 367, to which American U.S. Pat. No. 5,868,178 corresponds, proposes a three-part stopper in which the length of the outer plug is at least twice the length of the inner plug.

European patent application EP 0 873 726 proposes that the stopper is formed by a single-piece cylinder of hydrophobic microporous material.

French patent applications 2 771 285 and 2 784 572, to which American patent application US 2001/0014376 and American U.S. Pat. No. 6,416,611 correspond, propose that the stopper is constituted by a stiff insert perforated by a substantially coaxial orifice and a hydrophobic microporous membrane combined with the insert in order to seal the insert orifice on the inside.

French patent application 2 781 662, to which American U.S. Pat. No. 6,203,489 corresponds, proposes that the stopper is constituted by a fibrous plug comprising a compound of gelling material present in a gas-permeable dispersed form and comprising a compound of support fibres, with the compound of gelling material being finely distributed throughout the compound of support fibres, so as to allow the swelling of the gelling material after it is brought into contact with a substance containing water, in order to form a stopper integrated with the compound of support fibres. The gelling material is made from the same material as the powder of the conventional three-part stoppers. The gelling material swells by absorbing the water present in the liquid in order to completely fill the tube, and then it reaches a state of gelation while binding with the compound of support fibres in order to form an integrated stopper.

French patent applications 2 824 255 and 2 824 256, to which American patent applications US 2002/0183653 and US 2002/0188222 correspond, propose to add to the stopper, besides the powder and fibres, non-absorbent elements, namely a core made from thermoplastic material, covered with a sleeve made from braided threads, and non-absorbent material in dispersed form, in the powder.

PCT application WO 2010/070533 proposes that the stopper is made as a single-piece cylinder of sintered self-sealing microporous material as described for example in PCT application WO 2010/070533, i.e. constituted by a microporous matrix and particles of a substance with a high capacity for water absorption supported by the microporous matrix, which provides the unit with an intrinsic mechanical coherence (the particles do not become detached) even in the dampened state.

The purpose of the invention is to provide such a straw which is simple, convenient and economical to produce and which is efficient in use.

To this end the invention proposes a straw for the storage of a predetermined dose of a liquid-based substance containing water, in particular a biological substance, comprising a tube extending between a first end and a second end and comprising a liquid-tight, gas-permeable swelling plug, said swelling plug being arranged in the tube close to its first end and extending between a first end facing towards the first end of the tube and a second end facing towards the second end of the tube, said swelling plug comprising a fibrous support agent and a swelling agent combined with the support agent, said swelling agent swelling by absorption of water on contact with the liquid-based substance, with said swelling plug and said tube being configured so that after the liquid-based substance has come into contact with the swelling plug via its second end, the swelling plug blocks the passage of the liquid-based substance and by pushing on its first end, can be slid in the tube towards the second end of the tube;

characterized in that said swelling plug is configured, at least close to its second end, after the liquid-based substance has come up against its second end, to be in a state of swelling constrained by said tube such that if a first part of the swelling plug of a length comprised between 2 mm and 3 mm starting from the second end of the swelling plug has come out of the tube via the second end of the tube, whereas a second part of the swelling plug remains in the tube, the first part of the swelling plug becomes decompacted and expands with the second end of the swelling plug which assumes a diameter at least equal to one and a half times the inner diameter of the tube.

The part of the swelling plug that has come out of the tube expands because the tube no longer takes up the tension arising from the fact that the swelling has been constrained and because in the absence of this taking up of tension the part of the swelling plug that has come out of the tube becomes decompacted.

The invention is based on the observation that certain substances having a high water absorption capacity, in particular the superabsorbent polymers known as SAPs, although they are not bonding agents in the dampened state and on the contrary have a tendency to become virtually liquid as a result of the considerable quantity of water that they can absorb, can nevertheless act as a swelling agent in a swelling plug in order to form a straw stopper, if their swelling is suitably constrained by the tube of the straw.

It is in fact found that when the swelling is suitably constrained by the tube of the straw, the swelling agent can become so compact that it blocks the passage of the liquid and confers a mechanical strength on the swelling plug, whereas the support agent, which is simply fibrous, and the swelling agent, which has a tendency to become virtually liquid, cannot by themselves confer a mechanical strength on the swelling plug in the damped state. It will be noted in this regard that in the abovementioned part of the swelling plug that has come out of the tube, which has become decompacted, the swelling agent easily leaves the fibrous support agent, for example by simple wiping.

It was determined that the abovementioned features of expansion are present when the swelling plug has, close to its second end, a state of swelling which is suitably constrained by the tube.

The abovementioned expansion features serve only to reflect the state of swelling constrained by the tube. It is well understood that the straw according to the invention is used with the swelling plug which remains in the straw at its original location during storage of the substance, without coming out of the tube on completion of expulsion of the substance.

It will be noted that in the swelling plug of the straw described by French patent application 2 781 662, the cohesion of the swelling plug along the walls of the tube when the swelling plug is slid in the tube is maintained because the swelling agent in the dampened state becomes a bonding agent, so that the swelling plug becomes an integrated element.

It will also be noted that in the stopper made as a single-piece cylinder of sintered self-sealing microporous material described in the abovementioned PCT application WO 2010/070533, the cohesion of the stopper along the walls of the tube when the stopper is slid in the tube is maintained because the microporous matrix retains the substance having a high water absorption capacity.

In contrast, in the swelling plug of the straw according to the invention, without the state of constrained swelling, the fibrous support agent and the swelling agent cannot by themselves hold firmly to one another when the swelling agent has absorbed liquid. As stated previously, in the decompacted state, the swelling agent easily leaves the fibrous support agent, for example by simple wiping. It is the swelling constrained by the tube which ensures that the swelling agent is compacted and remains combined with the fibrous support agent.

It will be observed that the swelling plug of the straw according to the invention is likely to have swelling dynamics (speed of absorption of water) that are particularly high and in this case, albeit surprisingly, the swelling agent blocks the passage of the liquid-based substance so rapidly that the quantity of liquid-based substance consumed by the swelling plug is very small, unlike the swelling plug described by French patent application 2 781 662, in which the gelling material is made of the same material as the powder of the conventional three-part stoppers, so that performance in terms of the quantity of substance absorbed is similar to that of the conventional three-part stoppers.

It will be noted that the swelling plug of the straw according to the invention is relatively simple, convenient and economical to produce, and in any case much more than the single-piece cylinder of sintered self-sealing microporous material as described by PCT application WO 2010/070533.

Finally, it will be noted that the state of constrained swelling of the swelling plug results in the swelling plug being maintained in position relatively firmly with respect to the tube of the straw, and in any case much more than can be achieved with the single-piece cylinder of sintered self-sealing microporous material described by PCT application WO 2010/070533.

According to advantageous features of implementation of the straw according to the invention:

the swelling plug is a braid formed by combining threads;

the swelling plug comprises between eight and eleven threads per $mm^2$ of cross-section of the tube of the straw;

the swelling plug has a weight comprised between 0.8 and 1.2 mg per mm of length;

the swelling plug comprises a proportion by weight of swelling agent comprised between 20% and 30%;

the swelling agent is a superabsorbent polymer configured to absorb several hundred times its volume of water;

the swelling agent is sodium polyacrylate;

the swelling plug is formed by combining threads each comprising support fibres and swelling fibres, said support agent being formed by the support fibres and said swelling agent being formed by the swelling fibres;

the swelling plug has a first predetermined colour in the absence of prior contact with the liquid-based substance and a second predetermined colour, having a hue different from the hue of the first colour, when it has been in contact with said substance;

the swelling plug comprises a salt that is non-fluorophore in the dry state and fluorophore when it is dissolved in water;

said salt forms part of the group comprising a fluorescein salt, a Rhodamine B salt, a Rhodamine 6G salt and a salt of Eriochrome® Cyanine R;

the straw also comprises a gas- and liquid-permeable barrier plug extending between a first end facing towards the first end of the tube and a second end facing towards the second end of the tube, with the second end of the swelling plug and the first end of the barrier plug being arranged one against the other, said swelling plug and said barrier plug forming a stopper extending between the first end of the swelling plug and the second end of the barrier plug;

the barrier plug is a braid formed by combining threads and the swelling plug is a braid formed by combining threads, with the barrier plug comprising more threads than the swelling plug;

the barrier plug is formed by combining the threads each comprising fibres and a coating for rendering the thread hydrophobic; and/or said coating for rendering the thread hydrophobic comprises a fluorinated resin.

The disclosure of the invention will now be continued with the description of embodiments given below, for the purposes of illustration and non-limitatively, with reference to the attached drawings in which:

FIG. 1 is a diagrammatic view in longitudinal section of a straw according to the invention, in the empty state;

FIG. 2 is a view similar to FIG. 1 but showing the straw in the filled state;

FIG. 3 is a view similar to FIG. 2, but showing the straw after the dose of substance which was packaged therein has been expelled;

FIG. 4 is a view similar to FIG. 3, but showing the state assumed by the stopper when it has come partially out of the tube in a predetermined fashion;

FIG. 5 is a diagrammatic cross-sectional view of the swelling plug comprised by the stopper of the straw;

FIG. 6 is a diagrammatic cross-sectional view of one of the threads which form the swelling plug;

FIG. 7 is a diagrammatic cross-sectional view of the barrier plug comprised by the stopper of the straw;

FIG. 8 is a diagrammatic cross-sectional view of one of the threads which form the barrier plug;

FIGS. 9 to 12 are views similar to FIGS. 1, 2, 5 and 7 for a first variant of the straw according to the invention; and FIGS. 13 to 14 are views similar to FIGS. 2 and 6 for a second variant of the straw according to the invention.

The straw 10 shown in FIG. 1 comprises a tube 11 and a stopper 12.

The tube 11 is conventionally made from extruded plastic material, here transparent, with an inner diameter which is here of the order of 1.6 mm and a length of the order of 133 mm.

The outer diameter of the tube 11 is of the order of 2 mm.

The tube 11 extends between an end 13 and an end 14.

The stopper 12 is formed by a swelling plug 15 and by a barrier plug 16.

The swelling plug 15 extends between an end 17 facing towards the end 13 of the tube 11 and an end 18 facing towards the end 14 of the tube 11.

The barrier plug 16 extends between an end 19 facing towards the end 13 of the tube 11 and an end 20 facing towards the end 14 of the tube 11.

The end 18 of the swelling plug 15 and the end 19 of the barrier plug 16 are arranged one against the other.

The stopper 12 extends between the end 17 of the swelling plug 15 and the end 20 of the barrier plug 16.

As will be described below in more detail, the swelling plug 15 comprises a fibrous support agent and a swelling agent combined with the fibrous support agent, said swelling agent swelling by absorption of water on contact with a liquid containing water, as a result of which the swelling plug 15 is gas-permeable and liquid-tight.

It will be noted that the swelling plug 15 is capable of performing the same function as the conventional three-part stopper, but that the production of the straw is simpler and more convenient as it is sufficient to insert the swelling plug 15 into the tube 11 (and not a first fibrous plug, then the gelling powder and then a second fibrous plug).

The barrier plug 16 is fibrous. It is gas- and liquid-permeable.

In the initial state, shown in FIG. 1, the stopper 12 is arranged close to the end 13 of the tube 11 and it is provided that in the filled state, the dose of substance 22 (FIG. 2) which is to be stored in the straw 10 is placed between the stopper 12 and the end 14 of the tube 11 furthest from the stopper 12. The substance 22 is based on liquid containing water.

In order to fill the straw 10, the end 13 is placed in communication with a vacuum source while the end 14 is placed in communication with a vessel containing the substance 22 to be introduced into the straw.

The air initially contained between the stopper 12 and the end 14 is sucked through the stopper 12 while the substance 22 moves forward in the tube 11 until it comes up against the stopper 12, via the end 20 of the barrier plug 16 facing towards the end 14 of the tube 11, i.e. via the end of the stopper 12 shown on the right in FIGS. 1 and 2.

The substance 22 passes through the barrier plug 16 and comes up against the swelling plug 15 via its end 18 facing towards the end 14 of the tube 11, i.e. via the end shown on the right in FIGS. 1 and 2.

On contact with the substance 22, an area 23 of the swelling plug 15 situated close to its end 18 assumes a state of swelling constrained by the tube 11 which blocks the passage of the substance 22.

The straw 10 is then in the filled state shown in FIG. 2.

It will be observed that the area 23 of swelling constrained by the plug 15 is relatively short, here of the order of 3 mm starting from the end 18.

It is in fact found that the swelling dynamics of the swelling plug 15 on contact with the liquid-based substance 22 is such that a state of constrained swelling that is sufficient to block the passage of the liquid is reached when the swelling takes place only over a relatively short distance starting from the end 18, here of the order of 3 mm.

Albeit surprisingly, using a swelling agent with fast swelling dynamics, i.e. capable of absorbing a large quantity of liquid very rapidly, does not result in the swelling plug 15 absorbing a large quantity of the liquid-based substance 22, but on the contrary, given the speed with which is reached the state of constrained swelling allowing the passage of the liquid to be blocked, the quantity of liquid absorbed is relatively moderate, for example of the order of 3% of the dose of the substance 22 introduced into the straw 10.

It will be noted that the state of swelling constrained by the tube 11, assumed by the swelling plug 15, results in the swelling plug 15 being maintained relatively firmly in position with respect to the tube 11 of the straw 10.

In particular, the plug 15 can be maintained during handling of the straw 10 in the filled state, and remain in place in the tube 11 during freezing of the substance 22.

If necessary, after filling, the straw is welded close to one or both of its ends 13 and 14 and is stored cold.

In order to empty the straw 10, if necessary after cutting off the welded end portions and thawing, a rod 25 (FIG. 3) is inserted into the tube 11, coming to rest against the end 17 of the swelling plug 15, i.e. against the end of the plug 12 shown on the left in FIGS. 1 to 3.

Using this rod, the plug 12 is made to slide in the manner of a piston towards the end 14, which causes the expulsion of the dose of substance 22 which had been introduced into the straw.

The end 14 is in the initial location or is set back with respect to the initial location if the tube 11 had been welded and the welded portion had been cut off before the expulsion of the dose of substance 22.

FIG. 3 shows the straw 10 on completion of the expulsion of the dose of substance 22. The end 20 of the barrier plug 16, which here forms the end of the stopper 12 facing towards the end 14 of the tube 11, is level with the end 14.

If the rod 25 is further pushed onto the stopper 12, the barrier plug 16 leaves the tube 11 then the swelling plug 15 in turn comes out of the tube 11.

In the configuration shown in FIG. 4, a part 26 of the swelling plug 15 has been brought out of the tube 11. Here, the length l of the part 26 is of the order of 2 mm.

By providing that the part 26 of the swelling plug 15 brought out of the tube 11 has a length l comprised between 2 and 3 mm, it is ensured that the part 26 belongs entirely to the area 23 of constrained swelling, which has a length of the order of 3 mm.

As soon as it comes out of the tube 11, the part 26 is decompacted. Decompaction takes place because the tube 11 no longer takes up the tension arising from the fact that the swelling has been constrained. Due to the decompaction, the end 18 assumes a generally convex shape and the lateral surface of the part 26 assumes a generally frustoconical shape. This is how the part 26 expands. Once the expansion is complete, the end 18 has a contour which has here a diameter d of the order of 4 mm.

It will be noted that the part 26 of the swelling plug 15 is described above and is shown very diagrammatically in FIG. 4. Due to the fact that the part 26 of the swelling plug 15 is decompacted, its actual contour displays irregularities around the general contour described and shown.

In practice, the configuration shown in FIG. 4 can be obtained by placing the straw 10, after the latter has been emptied as shown in FIG. 3, on a horizontal surface and by pushing the stopper 12 until the swelling plug 15 has come out of the tube 11 over the length l from the end 18. In order to facilitate measurement of the length l, the horizontal surface is for example formed by a sheet of millimeter-squared paper.

Placing the straw 10 on the horizontal surface has no effect, or only a slight effect, on the shape assumed by the part 26, since the part 26 is decompacted after coming out of the tube 11.

As already stated, in the decompacted state assumed by the part 26, the swelling agent easily leaves the support agent.

If, starting from the configuration shown in FIG. 4, the straw 10 is rolled on the surface on which it rests, swelling agent is deposited on the surface as a result of the part 26 being rolled thereon.

The barrier plug 16 is useful in the straw 10 to ensure that the swelling agent in the dampened state remains in the swelling plug 15: the barrier plug 16 prevents it from passing towards the substance 22.

It will be noted that when the barrier plug 16 is in the tube 11, it is slightly compressed and that it therefore decompresses slightly when it is outside the tube 11 as shown in FIG. 4.

Here, the diameter of the barrier plug 16 outside the tube 11 is a few hundredths of a mm greater than the inner diameter of the tube 11.

The swelling plug 15 will now be described in detail, with reference to FIGS. 5 and 6.

The swelling plug 15 is a braid formed by combining threads 32 (FIG. 6). Here, the swelling plug 15 is formed by nineteen identical threads arranged in a core 30 and a cover 31 surrounding the core 30.

The core 30 is formed by three threads placed parallel, against one another.

The cover 31 has an annular cross section. It is formed by sixteen braided threads distributed in eight strands each comprising two threads.

One of the threads 32 which form the swelling plug 15 is shown very diagrammatically in cross section in FIG. 6.

The thread 32 comprises support fibres 33 and swelling fibres 34.

The support fibres 33 and the swelling fibres 34, in order to produce the thread 32, are assembled in a well-known manner by twist spinning.

Here, the support fibres 33 are discontinuous filaments of polyester and/or of viscose, neither cracked nor carded; and the swelling fibres 34 are discontinuous filaments of sodium polyacrylate, neither cracked nor carded.

Sodium polyacrylate is a superabsorbent polymer (SAP) capable of absorbing several hundred times its own volume of water.

It will be noted that sodium polyacrylate is not spermicidal and therefore is suitable for contact with animal semen.

The swelling fibres 34 have here a length of 6 mm at most.

The support fibres 33 are relatively aerated. This allows them to be gas-permeable.

Moreover, the aerated character of the support fibres 33 means that the thread 32 has a fluffy contour, which is favourable to maintaining the swelling plug 15 in the tube 11 when the straw is in the empty state (swelling plug 15 in the dry state).

The support fibres 33 occupy a relatively large volume in the thread 32 with respect to the volume occupied by the fibres 34, which are relatively compact.

This arrangement is favourable to the speed of absorption of liquid by the threads 32: the aerated character of the support fibres 33 and the large volume occupied by the support fibres 33 allow each thread 32 to be wetted by a large quantity of liquid and thus to feed the swelling fibres 34 very rapidly with liquid.

In the swelling plug 15 formed by combining threads 32 arranged as already indicated (core 30 and cover 31), the fibrous support agent is formed by the support fibres 33 of the threads 32 and the swelling agent is formed by swelling fibres 34 of the threads 32.

As already indicated, if, starting from the configuration shown in FIG. 4, the straw 10 is rolled on the surface on which it rests, swelling agent is deposited on the surface as a result of the part 26 being rolled thereon.

In the swelling agent deposited on the surface, there are rod-shaped elements which are swelling fibres 34 that have absorbed a large quantity of liquid.

Here, in the dry state, the thread 32 comprises 75% support fibres 33 and 25% swelling fibres 34 by weight.

As a result, the swelling plug 15, in the dry state, comprises 75% fibrous support agent and 25% swelling agent.

It is understood that in order for the swelling plug to remain in the dry state, the humidity of the ambient air must remain less than 50%.

It will be observed that the proportion of 25% swelling agent is relatively low.

Albeit surprisingly, it was determined that the swelling dynamics of the swelling plug 15 are better (more rapid swelling) than with a much higher proportion by weight, such as 45%. This probably originates from the fact that with a higher proportion by weight there is a smaller exchange surface such that the liquid takes a longer time to reach the swelling agent.

Generally, it was determined that the swelling plug offers good swelling dynamics when the proportion of swelling agent is comprised between 20% and 30% by weight.

In practice, it is possible to find the content of swelling agent in the swelling plug 15 by weighing it in the dry state (as delivered in a straw in the empty state) then placing the swelling plug 15 in a water-permeable casing so that the threads remain grouped together, then washing the assembly in order to remove the swelling agent (which is virtually liquid in the dampened state and which is therefore removed by washing) then weighing the remaining threads in the dry state, which threads then comprise the only fibrous support agent.

Here, the swelling plug 15 has a dry weight of the order of 1.07 mg per mm of length.

It has generally been determined that the swelling plug 15 performs very well when it has a weight comprised between 0.8 and 1.2 mg per mm of length.

The barrier plug 16 will now be described in detail, with reference to FIGS. 7 and 8.

The barrier plug 16 is a braid which is here formed by thirty-two identical threads arranged in a core 35 and a cover 36 surrounding the core 35.

The core 35 is formed by two threads arranged parallel, against one another.

The cover 36 has an annular cross section. It is formed by thirty braided threads divided into six strands each comprising two threads and six strands each comprising three threads.

One of the threads 37 which form the barrier plug 16 is shown very diagrammatically in cross section in FIG. 8.

The thread 37 is formed from fibres 38 similar to the support fibres 33 of the thread 32 and by a coating 39 rendering the thread 37 hydrophobic.

Here, the coating 39 is of fluorinated resin.

Due to the fact that the threads 37 are rendered hydrophobic by the coating 39, the barrier plug 16 has a water-repellant effect.

This repellant effect does not prevent the substance 22 from passing through the barrier plug 16 and reaching the swelling plug 15, since in practice the substance 22 comes up against the stopper 12 with a certain speed.

During the passage of the substance 22 in the barrier plug 16, the threads 37 do not absorb liquid; and after the area 23 of constrained swelling of the swelling plug 15 is formed and the passage of the liquid-based substance is blocked, the barrier plug 16 does not keep the liquid situated in its interstices but returns it into the dose of liquid substance situated between the end 20 of the barrier plug 16 and the end 14 of the tube 11.

As a result, there is no consumption, or very reduced consumption, of liquid substance by the barrier plug 16.

The variant of the straw 10 shown in FIGS. 9 and 10 is similar to the straw 10 which has just been described with reference to FIGS. 1 to 8, except that:

the swelling plug 15 is shorter, here with a length (distance between its ends 17 and 18) which is of the order of 3 mm;

the tube 11 has a larger inner diameter, here of the order of 2.5 mm; and similarly, the swelling plug 15 and the barrier plug 16 have a larger diameter.

The outer diameter of the tube 11 is of the order of 3 mm.

Here, the swelling plug 15 of the straw 10 shown in FIGS. 9 and 10 is made with the same threads 32, but in greater numbers, than the swelling plug 15 of the straw 10 shown in FIGS. 1 to 4.

More precisely, as shown in FIG. 11, the swelling plug 15 of the straw 10 shown in FIGS. 9 and 10 is here a braid formed by forty-eight identical threads arranged in a core 30 formed by sixteen braided threads divided into twelve strands each comprising two threads and in a cover 31 with an annular cross section, surrounding the core 30, formed by twenty-four braided threads divided into twelve strands each comprising two threads.

Here, the barrier plug 16 is made with threads 37 that are similar to, but thicker than, the threads 37 of the barrier plug 16 of the straw 10 shown in FIGS. 1 to 4.

More precisely, as shown in FIG. 12, the barrier plug 16 of the straw 10 shown in FIGS. 9 and 10 is here a thread formed by twenty-eight identical threads arranged in a core 35 formed by four threads arranged parallel against one another, and in a cover 36 with an annular cross section surrounding the core 35, formed by twenty-four threads divided into twelve strands each comprising two threads.

Due to the fact that the swelling plug 15 has a length (distance between its ends 17 and 18) which is of the order of 3 mm, the area 23 of constrained swelling, which here is also of the order of 3 mm, extends as shown in FIG. 10, over the entire length of the swelling plug 15.

A part of the swelling plug 15 that has come out of the tube 11 over a length of the order of 2 mm starting from the end 18, expands like the part 26 shown in FIG. 4.

Once the expansion is completed, the end 18 has a contour which here has a diameter d of the order of 6 mm.

Generally, by providing that the part of the swelling plug 15 which has come out of the tube 11 has a length l comprised between 2 and 3 mm, it is ensured that the part that has come out of the tube 11 belongs in its entirety to the area 23 of constrained swelling, which has a length of the order of 3 mm.

In order to observe the expansion, a part of the swelling plug 15 should be kept in the tube 11. For example, with the plug 15 of the straw 10 shown in FIGS. 1 to 4, the part that has come out of the tube can have a length l of 3 mm since the swelling plug 15 is longer. With the swelling plug 15 of the straw 10 shown in FIGS. 9 and 10, the part that has come out of the tube must have a length that is smaller than 3 mm (this is the length of the swelling plug 15).

It will be noted that the braiding of the threads 32 which form the swelling plug 15 allows the threads 32 to be held one against another, but that close to the ends the threads 32 can quite easily become unbraided and separated from one other.

The part of the swelling plug 15 that has come out of the tube, both in the case of the straw 10 shown in FIGS. 1 to 4 and in the case of the straw 10 shown in FIGS. 9 and 10, is close to the end 18. The braiding of the threads 32 thus does not prevent the threads 32, or more precisely what remains of them after swelling of the swelling fibres 34, to become separated from one another.

In practice, generally, the end such as 18 of the part such as 23, having a length comprised between 2 mm and 3 mm starting from the end such as 18, expands with the end such as 18 which adopts a diameter which can reach up to three times the inner diameter of the tube.

Generally, it was determined that the straw such as 10 performs very well when the part such as 23 of the swelling plug such as 15, that has a length comprised between 2 mm and 3 mm starting from the end such as 18, expands with the end such as 18 which assumes a diameter at least equal to one and a half times the inner diameter of the tube.

For example, in the case of the straw 10 shown in FIGS. 1 to 4, the inner diameter of which is of the order of 1.6 mm, the diameter of the end 18 is at least equal to 2.4 mm; and in the case of the straw 10 shown in FIGS. 9 and 10, the inner diameter of which is of the order of 2.5 mm, the diameter of the end 18 is at least equal to 3.7 mm.

The swelling of the swelling agent is then suitably constrained by the tube 11.

In having its swelling thus constrained by the tube 11, the swelling agent of the swelling plug 15 becomes so compact that it blocks the passage of the liquid-based substance 22 while it confers a mechanical strength on the area 23 of constrained swelling.

In particular, the swelling plug 15 remains consistent (the swelling agent and the fibrous support agent are held one against the other) when the swelling plug 15 is slid in the tube 11 in order to empty the straw 10.

It will be noted that the blocking of the liquid-based substance 22 achieved by the swelling plug 15, which takes place particularly rapidly as explained above, is particularly suitable for carrying out the filling of the straws 10 with an automatic machine, the operating speed of which may be very high, up to several thousand straws per hour.

In the straw 10 shown in FIGS. 9 and 10, the fact that the stopper is shorter makes it possible to maximize the space available for storage of the liquid-based substance.

It will be noted that that in the straw 10 shown in FIGS. 1 to 4, the length of the stopper 12, i.e. the distance between the end 17 of the swelling plug 15 and the end 20 of the barrier plug 16 is of the order of 10 mm, and that the distance between the end 14 of the tube 11 and the end 17 of the swelling plug 15 is of the order of 7 mm.

The straw 10 shown in FIGS. 1 to 4 can therefore be used in exactly the same way as a conventional straw. In particular, in order to be emptied, it can be placed in a conventional insemination gun.

It will be observed that in the straw 10 shown in FIGS. 1 to 4, of which the inner diameter of the tube is of the order of 1.6 mm, and of which the inner cross section of the tube is therefore of the order of 2 mm$^2$, the swelling plug 15 comprises nineteen threads 32 i.e. 9.5 threads per mm$^2$ of cross section of the tube and that, in the straw 10 shown in FIGS. 9 and 10, of which the inner diameter of the tube is of the order of 2.5 mm, and of which the inner cross section of the tube is therefore of the order of 5 mm$^2$, the plug 15 comprises forty-eight threads i.e. 9.6 threads per mm$^2$ of cross section of the tube.

It has generally been determined that the swelling plug 15 performs very well when there are between 8 and 11 threads per mm$^2$ of cross section of the tube of the straw.

With the exception of the coating 39 of the threads 37, the barrier plug 16 of the straw 10 shown in FIGS. 1 to 4 and the barrier plug 16 of the straw 10 shown in FIGS. 9 and 10 are generally configured like one of the fibrous plugs of a conventional three-part stopper.

As a variant, the barrier plug 16 is replaced by another similar barrier plug, the threads 37 of which do not comprise the coating 39 rendering them hydrophobic.

In this case, the barrier plug 16 has no repellant effect on the liquid.

Once the straw is filled, the swelling plug 15 continues to block the passage of the liquid-based substance 22 in a suitable manner for several hours, i.e. the usual time between the filling and freezing of the straw or its direct use for carrying out artificial insemination.

It is understood that the blocking of the passage of the liquid-based substance 22 by the swelling plug 15 is neither absolute nor permanent.

For example, if the straw 10 is left in the filled state at ambient temperature beyond a few hours, i.e. outside the usual conditions of use of a straw, a small quantity of liquid-based substance is likely to spread in the swelling plug 15 beyond the area 23 of constrained swelling, probably by capillary action, along the threads 32.

When the straw is frozen, it is no longer necessary to block the passage of the substance 22, which is then in a solid state.

The variant of the straw 10 shown in FIG. 13 is similar to the straw 10 shown in FIGS. 1 to 4, except that the threads 32 which form the swelling plug 15, shown in FIG. 14, are similar to the thread 32 shown in FIG. 6 but comprise a coating 40 that changes hue between the dry state and the dampened state.

In the empty state, the swelling plug 15 of the straw 10 shown in FIG. 13 has the same appearance as the swelling plug 15 of the straw 10 shown in FIG. 1.

In the filled state, the area 23 of constrained swelling of the plug 15 of the straw shown in FIG. 13 has a different appearance to that of the plug 15 in the dry state.

More precisely, when the straw 10 shown in FIG. 13 is in the empty state, the swelling plug 15 has a first colour and when this straw 10 is in the filled state shown in FIG. 13, the dampened part of the swelling plug 15 (area 23 of constrained swelling) has a second colour.

Here, the hue of the first colour (empty state) is brownish white while the hue of the second colour (filled state) is greenish yellow.

For example, the swelling plug 15 when the straw is in the empty state, as viewed through the tube 11, has a Pantone® 155U colour and the area 23 of the swelling plug 15 when the straw is in the filled state (FIG. 13), as viewed through the tube 11, has a Pantone® 395C colour.

It is recalled here that the hue of a colour corresponds to the wavelengths (or to the single wavelength in the case of a colour of the rainbow) of the light emitted by the object having this colour. The hue is only one of the components of the colour, which depends on other parameters such as luminosity and saturation.

The change in hue of the swelling plug 15 between the dry state and the dampened state is due to the presence of the hue-change coating 40.

Here, the coating 40 is a fluorescein sodium salt.

It will be noted that the fluorescein sodium salt is not spermicidal and therefore is suitable for contact with animal semen.

It is known that the fluorescein sodium salt has the following formula:

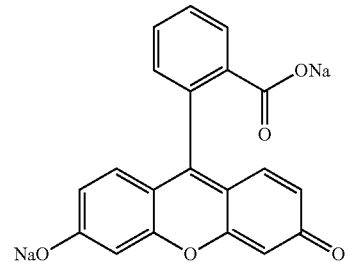

and that it is identified by CAS number 518-47-8.

It is also known that the fluorescein sodium salt is a fluorophore salt i.e. capable of emitting fluorescent light when it is dissolved in water; while in the dry state it is a non-fluorophore salt.

When the swelling plug 15 of the straw 10 shown in FIG. 13 is in the dry state, the fluorescein sodium salt does not emit fluorescent light as it is in the dry state. When this swelling plug is in the dampened state, the fluorescein sodium salt is dissolved in the water contained in the portion 33 and then emits fluorescent light.

The change in hue of the portion 23 of the swelling plug 15 is due to the addition of fluorescent light.

Thanks to the presence of the fluorescein sodium salt, the swelling plug 15 forms a component that is an indicator of contact between the stopper 12 and the substance 22: the swelling plug 15 has a first predetermined colour in the absence of prior contact with the liquid-based substance 22 and a second predetermined colour, having a hue different from the hue of the first colour, when the swelling plug 15 has been in contact with the substance 22.

The component that is an indicator of contact with the substance 22, formed by the swelling plug 15, is useful for checking the correct filling of the straw 10, and more precisely the correct dampening of the stopper 12 by the substance 22.

Controlling the correct filling of the straw can be carried out visually by the operator, simply by checking that the swelling plug 15 of the stopper 12 has adopted the hue of the second predetermined colour, i.e. a greenish yellow hue in the present example.

The correct filling of the straw 10 can also be checked automatically.

In a variant of the swelling plug 15, the coating 40 of fluorescein sodium salt in the dry state is replaced by another product that is not fluorophore in the dry state and is fluorophore when it is dissolved in water, which is in the form of a salt in the dry state.

This is for example another fluorescein salt, a Rhodamine B salt, a Rhodamine 6G salt and/or a salt of Eriochrome® Cyanine R.

It is known that Rhodamine B has the following formula:

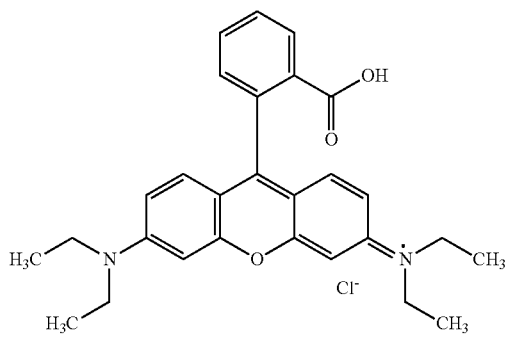

and that it is identified by CAS number 81-88-9.

It is known that Rhodamine 6G has the following formula:

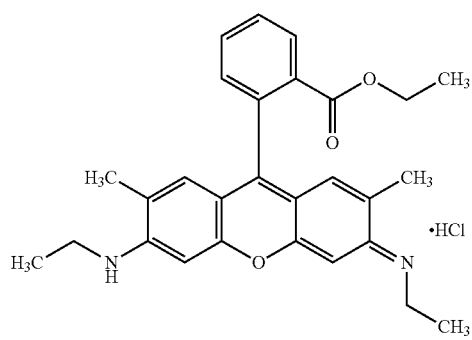 [SMILES: CC/N=c1\cc2oc3cc(NCC)c(C)cc3c(-c3ccccc3C(=O)OCC)c-2cc1C ; Cl]

and that it is identified by CAS number 989-38-8.

It is known that Eriochrome® Cyanine R has the following formula:

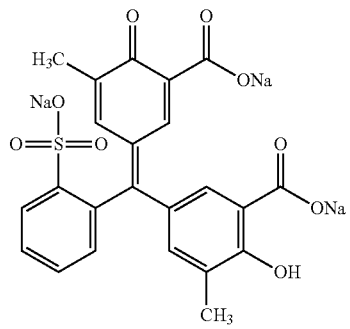

and that it is identified by CAS number 64-18-9.

By selecting one or more of these products, the hue of the swelling plug 15 can be adjusted in the dampened state.

In other variants, the agent such as the coating 40 modifying the colour of the swelling plug 15 is a colorant, without being fluorophore.

The colour-modifying agent being a colorant without being fluorophore is for example methylene blue or α-zurine.

Such colorant products, when they are in the dry state, has no effect, or only a slight effect, on the colour of the other products forming the swelling plug 15. However, when the swelling plug 15 is dampened, the colorant product communicates its coloration to the rest of the swelling plug 15.

In other variants, the change in colour of the swelling plug 15 is brought about on contact with a liquid other than water, for example a product contained in a diluent or a semen preservative for animal semen.

In other variants, the material of the tube such as 11 is not transparent, but translucent, for example slightly coloured.

In variants that are not shown, the threads 32 of the swelling plug 15 are different from the threads shown in FIGS. 6 and 14, with for example the integration of the swelling agent being carried out by coating of fibres such as the support fibres 33, for example by soaking of threads made from such support fibres or by hot coating, or also by coextrusion of multi-filament support fibres and a single-filament swelling fibre, or also by close mixing of multi-filament support fibres with a single-filament swelling fibre.

In other variants (not shown), the swelling plug 15 has different lengths, for example longer or shorter than the swelling plug 15 of the straw 10 shown in FIGS. 1 to 4.

In other variants (not shown), the stopper 12 is formed solely by the swelling plug 15 (there is no barrier plug 16).

In other variants (not shown), the threads such as 32 forming the swelling plug such as 15 are combined otherwise than by braiding, for example by stranding; and/or the support fibres 33 are made from a material other than polyester and/or viscose, for example polyamide or polypropylene.

Numerous other variants are possible depending on circumstances and it is recalled in this regard that the invention is not limited to the examples described and shown.

The invention claimed is:

1. A straw for the storage of a predetermined dose of liquid-based substance (22) containing water, in particular a biological substance, comprising a tube (11) extending between a first end (13) and a second end (14) and comprising a gas-permeable, liquid-tight swelling plug (15), said swelling plug (15) being arranged in the tube (11) close to the first end (13) and having a first end (17) facing towards the first end (13) of the tube (11) and a second end (18)

facing towards the second end (14) of the tube (11), said swelling plug (15) comprising a fibrous support agent and a swelling agent combined with the support agent, said swelling agent configured to cause the swelling plug (15) to swell upon absorption of water on contact with the liquid-based substance (22), with said swelling plug (15) and said tube (11) being configured so that after that the liquid-based substance (22) has come up against the swelling plug (15) via the second end (18), the swelling plug (15) blocks the passage of the liquid-based substance (22) and by pushing on the first end (17) can be slid in the tube (11) towards the second end (14) of the tube (11);

wherein the straw has an initial state in which a stopper (12) comprising the swelling plug (15) is arranged close to the second end (14) and a filled state in which the liquid-based substance (22) is placed between the stopper (12) and the second end (14) of the tube (11), wherein in the filled state, said swelling plug (15) is configured, at least close to the second end (18), after the liquid-based substance (22) has come up against the second end (18), to be in a state of swelling constrained by said tube (11), such that when a first part (26) of the swelling plug (15) of a length comprised between 2 mm and 3 mm starting from the second end (18) of the swelling plug (15) comes out of the tube (11) via the second end (14) of the tube (11), while a second part of the swelling plug (15) remains in the tube (11), the first part (26) of the swelling plug (15) becomes decompacted and expands with the second end (18) of the swelling plug (15) expanding to a diameter (d) at least equal to one and a half times the inner diameter of the tube (11).

2. The straw according to claim 1, wherein the swelling plug (15) is a braid comprising a combination of threads (32).

3. The straw according to claim 2, wherein the swelling plug (15) comprises between eight and eleven threads per mm$^2$ of cross section of the tube (11) of the straw (10).

4. The straw according to claim 1, wherein the swelling plug (15) has a weight comprised between 0.8 and 1.2 mg per mm of length.

5. The straw according to claim 1, wherein the swelling plug (15) comprises a proportion by weight of swelling agent comprised between 20% and 30%.

6. The straw according to claim 1, wherein the swelling agent is a superabsorbent polymer configured to absorb several hundred times its volume in water.

7. The straw according to claim 1, wherein the swelling agent is sodium polyacrylate.

8. The straw according to claim 1, wherein said swelling plug (15) comprises a combination of threads, each thread comprising support fibres (33) and swelling fibres (34), said support agent comprising the support fibres (33) and said swelling agent comprising the swelling fibres (34).

9. The straw according to claim 1, wherein the swelling plug (15) has a first predetermined colour in the absence of prior contact with the liquid-based substance (22) and a second predetermined colour, having a different hue from the hue of the first colour, when it has been in contact with said substance (22).

10. The straw according to claim 9, wherein said swelling plug (15) comprises a salt that is not fluorophore in the dry state and is fluorophore when it is dissolved in water.

11. The straw according to claim 10, wherein said salt forms part of the group comprising a fluorescein salt, a Rhodamine B salt, a Rhodamine 6G salt and a salt of Eriochrome® Cyanine R.

12. The straw according to claim 1, further comprising a gas- and liquid-permeable barrier plug (16) having a first end (19) facing towards the first end (13) of the tube (11) and a second end (20) facing towards the second end (14) of the tube (11), with the second end (18) of the swelling plug (15) and the first end (19) of the barrier plug (16) being arranged one against the other, and wherein said swelling plug (15) and said barrier plug (16) together comprise the stopper (12) extending between the first end (17) of the swelling plug (15) and the second end (20) of the barrier plug (16).

13. The straw according to claim 12, wherein the barrier plug (16) is a braid comprising a combination of first threads (37) and the swelling plug (15) is a braid comprising a combination of second threads (32), with the barrier plug (16) comprising more threads than the swelling plug (15).

14. The straw according to claim 1, wherein the barrier plug (16) comprises the first threads (37), each of the first threads (37) comprising fibres (38) and a coating (39) to render the thread (37) hydrophobic.

15. The straw according to claim 14, wherein said coating (39) for rendering the thread (37) hydrophobic comprises a fluorinated resin.

* * * * *